(12) United States Patent
Stearns

(10) Patent No.: US 7,103,233 B2
(45) Date of Patent: Sep. 5, 2006

(54) METHODS AND APPARATUS FOR DETERMINING COMPONENT ALIGNMENT

(75) Inventor: Charles William Stearns, New Berlin, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 741 days.

(21) Appl. No.: 10/284,659

(22) Filed: Oct. 31, 2002

(65) Prior Publication Data
US 2004/0086199 A1 May 6, 2004

(51) Int. Cl.
G06K 9/00 (2006.01)
G06K 9/36 (2006.01)
A61B 6/04 (2006.01)

(52) U.S. Cl. .......................... 382/289; 382/131; 378/4
(58) Field of Classification Search ........ 382/128–134, 382/289, 294–297; 378/205, 209; 600/407, 600/415
See application file for complete search history.

(56) References Cited

U.S. PATENT DOCUMENTS

| 5,097,132 | A | 3/1992 | Plummer | 250/363.08 |
|---|---|---|---|---|
| 5,178,146 | A | 1/1993 | Giese | 128/653.02 |
| 5,210,421 | A | 5/1993 | Gullberg et al. | 250/363.04 |
| 5,338,936 | A | 8/1994 | Gullberg et al. | 250/363.04 |
| 5,613,013 | A | 3/1997 | Schuette | 382/124 |
| 5,647,018 | A | 7/1997 | Benjamin | 382/128 |
| 5,741,215 | A | 4/1998 | D'Urso | 600/407 |
| 5,845,639 | A | 12/1998 | Hochman et al. | 128/653.1 |
| 5,871,013 | A | 2/1999 | Wainer et al. | 128/653.1 |
| 5,937,083 | A | 8/1999 | Ostuni | 382/131 |
| 6,161,031 | A | 12/2000 | Hochman et al. | 600/407 |
| 6,205,347 | B1 * | 3/2001 | Morgan et al. | 600/407 |
| 6,272,200 | B1 | 8/2001 | Pan et al. | 378/15 |
| 6,448,559 | B1 * | 9/2002 | Saoudi et al. | 250/367 |
| 6,490,476 | B1 | 12/2002 | Townsend et al. | 600/427 |
| 6,666,579 | B1 * | 12/2003 | Jensen | 378/197 |
| 6,754,520 | B1 * | 6/2004 | DeSilets et al. | 600/415 |
| 2002/0081008 | A1 | 6/2002 | Wollenweber | |
| 2003/0004405 | A1 | 1/2003 | Townsend et al. | |
| 2003/0058984 | A1 | 3/2003 | Susami et al. | |
| 2003/0063787 | A1 | 4/2003 | Natanzon et al. | |

* cited by examiner

Primary Examiner—Kanjibhai Patel
(74) Attorney, Agent, or Firm—Carl B. Horton, Esq.; Armstrong Teasdale LLP

(57) ABSTRACT

A method for determining component misalignment in a multi-modality imaging system including a first modality unit, a second modality unit, and a table, includes imaging an object with the first modality unit to generate a first image, imaging the object with the second modality unit to generate a second image, and determining a table alignment status using the first and second images.

21 Claims, 4 Drawing Sheets

METHODS AND APPARATUS FOR DETERMINING COMPONENT ALIGNMENT

BACKGROUND OF THE INVENTION

This invention relates generally to imaging systems capable of scanning objects in multi modalities and more particularly to a method for determining an alignment status of the multi-modality system.

The present invention is directed toward multi-modal imaging systems capable of scanning using different modalities, such as, for example, but not limited to, Positron Emission Tomography (PET) and Computed Tomography (CT). The difference between multi-mode and multi-modality is that in multi-mode systems the same hardware is utilized to perform scans in different modes (e.g., a radiation source and a radiation detector is used in both a flouro mode and a tomosynthesis mode), while in a multi-modal system (multi-modality system), although some of the same hardware is utilized to perform different scans (e.g., an image produced by PET is processed and displayed respectively, by the same computer and display, as an image produced by CT), the data acquisition systems (hereinafter sometimes termed "modality unit") are different. For example, on a CT/PET system, a radiation source and a radiation detector are used in tandem to acquire CT data, while a radiopharmaceutical is typically employed in tandem with a PET camera to acquire PET data. It is contemplated that the benefits of the invention accrue to all multi-modality imaging systems, such as, for example, but not limited to, a CT/PET imaging system as well as systems utilizing currently unknown modalities as well as currently unfeasible combinations, such as, for example, but not limited to, a combination PET/ultrasound system and/or a CT/MRI system.

In such multi-modality systems, such as, for example, an integrated PET-CT system there is an inherent registration of the PET and CT images the system acquires. Since the patient lies still on the same table during the PET and CT portions of the acquisition, the patient will be in a consistent position and orientation during the two acquisitions, greatly simplifying the process of correlating and fusing the CT and PET images. This allows the CT image to be used to provide attenuation correction information for the reconstruction of the PET image, and allows an image reader to easily correlate the anatomic information presented in the CT image and the functional information presented in the PET image.

This inherent registration assumes a perfect alignment of the PET and CT detector coordinate systems, or at least a known spatial transformation between the two coordinate systems. This should be readily apparent, since a misalignment of the coordinate systems will directly result in a misregistration of the images.

Proper PET and CT image registration also requires an alignment of the axial (z-) axis of the PET and CT coordinate systems not only with each other and with the travel axis of the table that transports the patient during the PET and CT acquisitions. This may be less obvious, but it is a consequence of the differing nature of the PET and CT acquisitions. A volume of CT image data is acquired slice-by-slice, or, in the case of a multislice helical scan, by a detector system with a small axial extent of a few centimeters. By contrast, a PET scan is acquired in a number of frames of data, each of which may cover an axial extent of 15 cm or more. Even if the CT and PET are perfectly aligned, a misaligned table will produce different artifacts in the CT and PET volumes, which cannot be properly registered. Accordingly it is desirable to provide a method for determining an alignment status of the multi-modality system.

BRIEF SUMMARY OF THE INVENTION

In one aspect, a method for determining component misalignment in a multi-modality imaging system is provided. The imaging system includes a first modality unit, a second modality unit, and a table. The method includes imaging an object with the first modality unit to generate a first image, imaging the object with the second modality unit to generate a second image, and determining a table alignment status using the first and second images.

In another aspect, a method for determining component misalignment in a Positron Emission Tomography/Computed Tomography (PET/CT) system is provided. The PET/CT system includes a PET unit, a CT unit, and a table. The method includes imaging an object with the PET unit to generate a first image, imaging the object with the CT unit to generate a second image, and determining a table alignment status using the first and second images.

In yet another aspect, a method for installing a Positron Emission Tomography/Computed Tomography (PET/CT) system at a desired location is provided. The PET/CT system includes a PET unit, a CT unit, and a table. The method includes positioning the PET/CT system at the desired location wherein the table has an axis extending through the system, imaging an object with the PET unit to generate a first image, imaging the object with the CT unit to generate a second image, and adjusting the table axis based upon the first and second images.

In one aspect, a multi modality imaging system includes a first modality unit including a bore therethrough, a second modality unit comprising a bore therethrough, and a table positioned to move at least partially through the first modality unit bore and the second modality bore. The system also includes a computer operationally coupled to the first and second modality units. The computer is configured to image an object with the first modality unit to generate a first image, image the object with the second modality unit to generate a second image, and calculate a matrix according to $$T \leftarrow \begin{pmatrix} N & 0 & 0 & 0 & -\sum z_P & -\sum y_P & 0 & 0 \\ 0 & N & 0 & \sum z_P & 0 & \sum x_P & 0 & 0 \\ 0 & 0 & N & -\sum y_P & \sum x_P & 0 & \sum x_P & -\sum y_P \\ 0 & \sum z_P & -\sum y_P & \sum y_P^2 + \sum z_P^2 & -\sum x_P y_P & \sum x_P z_P & -\sum x_P y_P & \sum y_P^2 \\ -\sum z_P & 0 & \sum x_P & -\sum x_P y_P & \sum x_P^2 + \sum z_P^2 & \sum y_P z_P & \sum x_P^2 & -\sum x_P y_P \\ -\sum y_P & \sum x_P & 0 & \sum x_P z_P & \sum y_P z_P & \sum x_P^2 + \sum y_P^2 & 0 & 0 \\ 0 & 0 & \sum x_P & -\sum x_P y_P & \sum x_P^2 & 0 & \sum x_P^2 & -\sum x_P y_P \\ 0 & 0 & -\sum y_P & \sum y_P^2 & -\sum x_P y_P & 0 & -\sum x_P y_P & \sum y_P^2 \end{pmatrix}$$

where N is the number of points in a first modality image space that match points in a second modality space, and $(x_p, y_p, z_p)$ are one of coordinates of points in an image space of the first image and coordinates of points in an image space of the second image.

In another aspect, a computer readable medium encoded with a program is provided. The program is configured to instruct a computer to image an object with a multi-modal imaging system in a first modality to generate a first image, image the object with the multi-modal imaging system in a second modality to generate a second image, and determine a table alignment status using the first and second images.

DETAILED DESCRIPTION OF THE INVENTION

Figure 1:
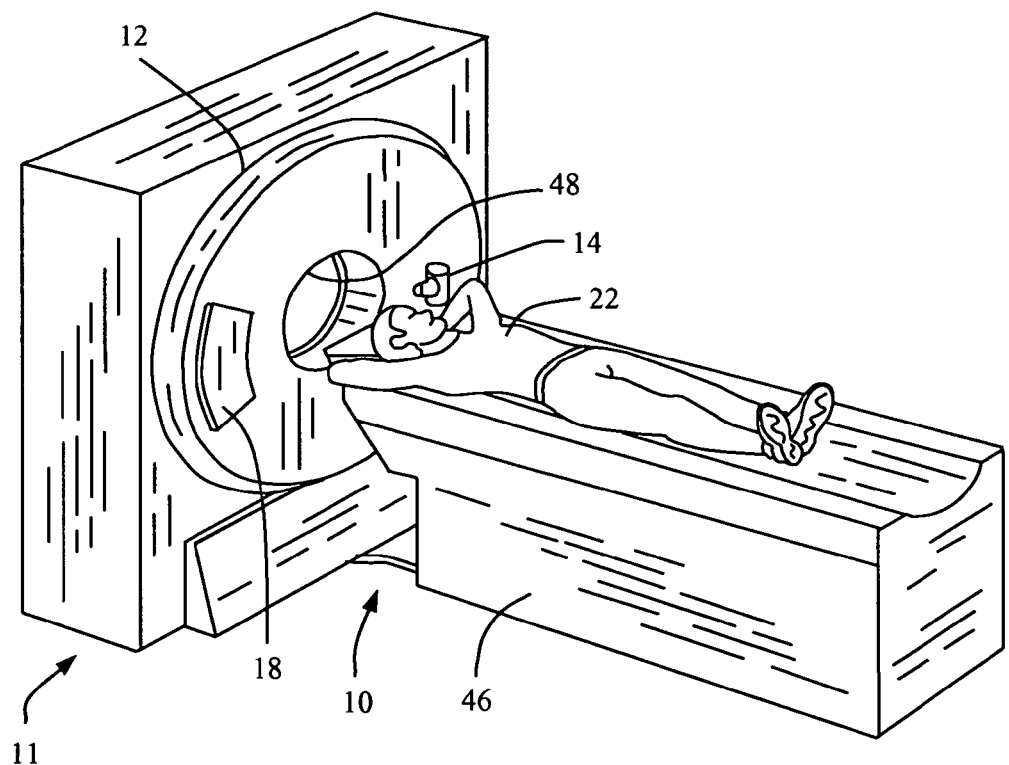
FIG. 1 is a pictorial view of a multi-modal imaging system.

In some known CT imaging system configurations, an x-ray source projects a fan-shaped beam which is collimated to lie within an X–Y plane of a Cartesian coordinate system and generally referred to as an "imaging plane". The x-ray beam passes through an object being imaged, such as a patient. The beam, after being attenuated by the object, impinges upon an array of radiation detectors. The intensity of the attenuated radiation beam received at the detector array is dependent upon the attenuation of an x-ray beam by the object. Each detector element of the array produces a separate electrical signal that is a measurement of the beam intensity at the detector location. The intensity measurements from all the detectors are acquired separately to produce a transmission profile.

In third generation CT systems, the x-ray source and the detector array are rotated with a gantry within the imaging plane and around the object to be imaged such that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector.

In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

To reduce the total scan time, a "helical" scan may be performed. To perform a "helical" scan, the patient is moved while the data for the prescribed number of slices is acquired. Such a system generates a single helix from a fan beam helical scan. The helix mapped out by the fan beam yields projection data from which images in each prescribed slice may be reconstructed.

Reconstruction algorithms for helical scanning typically use helical weighing algorithms that weight the collected data as a function of view angle and detector channel index. Specifically, prior to a filtered backprojection process, the data is weighted according to a helical weighing factor, which is a function of both the gantry angle and detector angle. The weighted data is then processed to generate CT numbers and to construct an image that corresponds to a two dimensional slice taken through the object.

At least some CT systems are configured to also perform Positron Emission Tomography (PET) and are referred to as CT/PET systems. Positrons are positively charged electrons (anti-electrons) which are emitted by radio nuclides that have been prepared using a cyclotron or other device. The radio nuclides most often employed in diagnostic imaging are fluorine-18 (18F), carbon-11 (11C), nitrogen-13 (13N), and oxygen-15 (15O). Radio nuclides are employed as radioactive tracers called "radiopharmaceuticals" by incorporating them into substances such as glucose or carbon dioxide. One common use for radiopharmaceuticals is in the medical imaging field.

To use a radiopharmaceutical in imaging, the radiopharmaceutical is injected into a patient and accumulates in an organ, vessel or the like, which is to be imaged. It is known that specific radiopharmaceuticals become concentrated within certain organs or, in the case of a vessel, that specific radiopharmaceuticals will not be absorbed by a vessel wall. The process of concentrating often involves processes such as glucose metabolism, fatty acid metabolism and protein synthesis. Hereinafter, in the interest of simplifying this explanation, an organ to be imaged including a vessel will be referred to generally as an "organ of interest" and the invention will be described with respect to a hypothetical organ of interest.

After the radiopharmaceutical becomes concentrated within an organ of interest and while the radio nuclides decay, the radio nuclides emit positrons. The positrons travel a very short distance before they encounter an electron and, when the positron encounters an electron, the positron is annihilated and converted into two photons, or gamma rays. This annihilation event is characterized by two features which are pertinent to medical imaging and particularly to medical imaging using photon emission tomography (PET). First, each gamma ray has an energy of approximately 511 keV upon annihilation. Second, the two gamma rays are directed in substantially opposite directions.

In PET imaging, if the general locations of annihilations can be identified in three dimensions, a three dimensional image of an organ of interest can be reconstructed for observation. To detect annihilation locations, a PET camera is employed. An exemplary PET camera includes a plurality of detectors and a processor which, among other things, includes coincidence detection circuitry.

The coincidence circuitry identifies essentially simultaneous pulse pairs which correspond to detectors which are essentially on opposite sides of the imaging area. Thus, a simultaneous pulse pair indicates that an annihilation has occurred on a straight line between an associated pair of detectors. Over an acquisition period of a few minutes millions of annihilations are recorded, each annihilation associated with a unique detector pair. After an acquisition period, recorded annihilation data can be used via any of several different well known back projection procedures to construct the three dimensional image of the organ of interest.

As used herein, an element or step recited in the singular and preceded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. Therefore, as used herein the term "image" broadly refers to both viewable images and data representing a viewable image. However, many embodiments generate (or are configured to generate) at least one viewable image.

Figure 2:
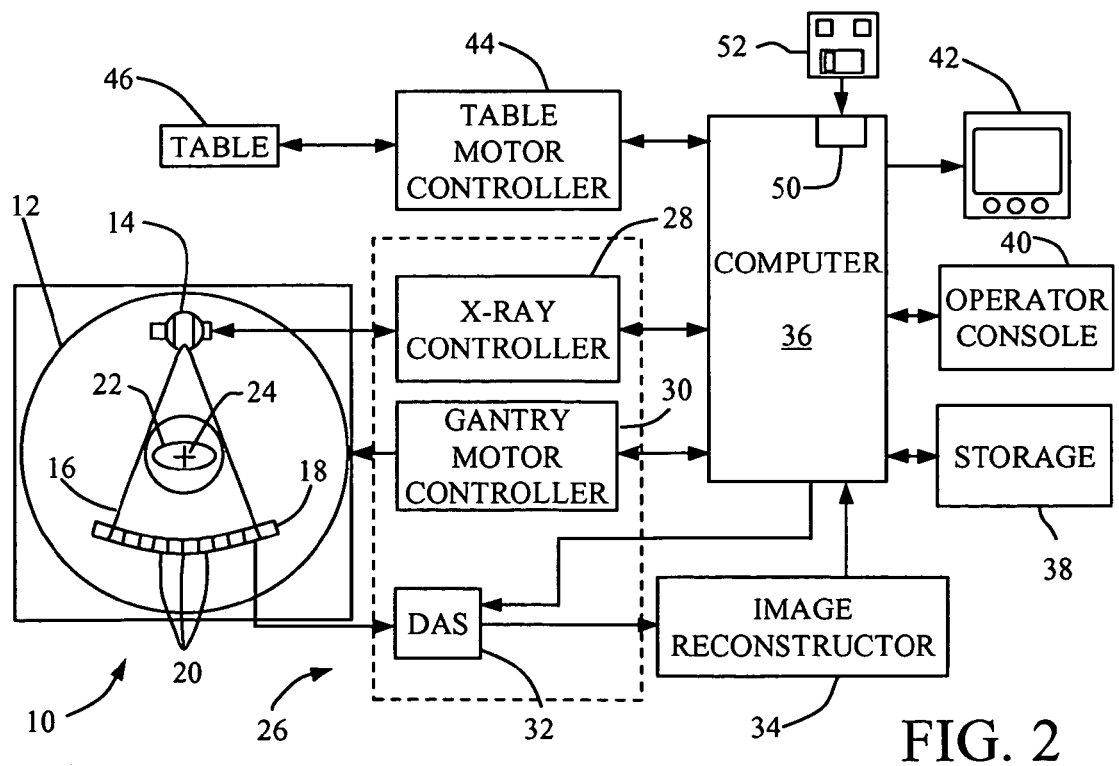
FIG. 2 is a block schematic diagram of the system illustrated in FIG. 1.

Referring to FIGS. 1 and 2, a multi-modal imaging system 10 is illustrated, and includes a first modality unit 11 and a second modality unit (not shown in FIGS. 1 and 2). The two modality units enable system 10 to scan an object in a first modality using the first modality unit and to scan the object in a second modality using the second modality unit. System 10 allows for multiple scans in different modalities to facilitate an increased diagnostic capability over single modality systems. In one embodiment, multi-modal imaging system 10 is a Computed Tomography/Positron Emission Tomography (CT/PET) imaging system 10, and CT/PET system 10 is shown as including a gantry 12 representative of a "third generation" CT imaging system in combination with PET circuitry. In alternative embodiments, modalities other than CT and PET are employed with system 10. Gantry 12 includes first modality unit 11 which has an x-ray source 14 that projects a beam of x-rays 16 toward a detector array 18 on the opposite side of gantry 12. Detector array 18 is formed by a plurality of detector rows (not shown) including a plurality of detector elements 20 which together sense the projected x-rays that pass through an object, such as a medical patient 22. Each detector element 20 produces an electrical signal that represents the intensity of an impinging x-ray beam and hence allows estimation of the attenuation of the beam as it passes through object or patient 22. During a scan to acquire x-ray projection data, gantry 12 and the components mounted thereon rotate about a center of rotation 24. FIG. 2 shows only a single row of detector elements 20 (i.e., a detector row). However, a multislice detector array 18 includes a plurality of parallel detector rows of detector elements 20 such that projection data corresponding to a plurality of quasi-parallel or parallel slices can be acquired simultaneously during a scan.

Rotation of gantry 12 and the operation of x-ray source 14 are governed by a control mechanism 26 of CT/PET system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high-speed image reconstruction. The reconstructed image is applied as an input to a computer 36 which stores the image in a storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

In one embodiment, computer 36 includes a device 50, for example, a floppy disk drive or CD-ROM drive, for reading instructions and/or data from a computer-readable medium 52, such as a floppy disk or CD-ROM. In another embodiment, computer 36 executes instructions stored in firmware (not shown). Computer 36 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein. CT/PET system 10 also includes a plurality of PET cameras including a plurality of detectors. The PET detectors and detector array 18 both detect radiation and are both referred to herein as radiation detectors. In one embodiment, CT/PET system 10 is a Discovery LS CT/PET system commercially available from General Electric Medical Systems, Waukesha Wis., and configured as herein described.

Additionally, although described in a medical setting, it is contemplated that the benefits of the invention accrue to all CT systems including industrial CT systems such as, for example, but not limited to, a baggage scanning CT system typically used in a transportation center such as, for example, but not limited to, an airport or a rail station.

Figure 3:
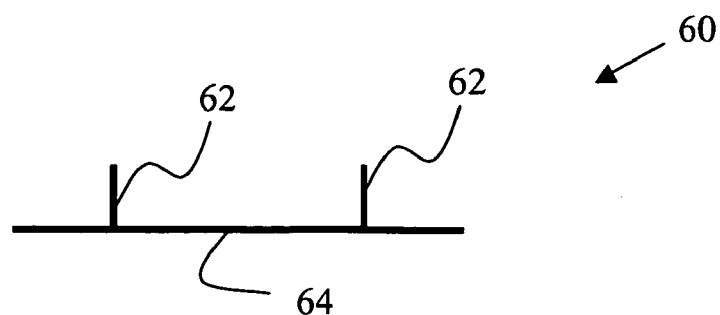
FIG. 3 illustrates a phantom.
Figure 4:
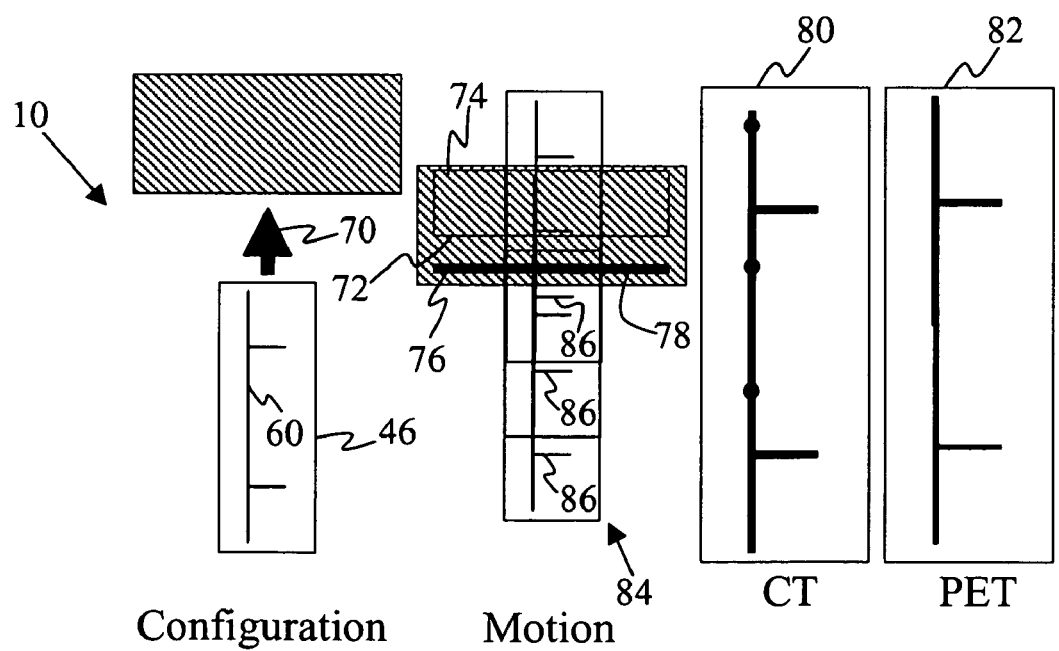
FIG. 4 illustrates the phantom aligned substantially perfect with an axis of the table shown in FIG. 1.

FIG. 3 illustrates a phantom 60 including two appendages 62 (arms) extending perpendicular to a body 64 of phantom 60. Appendages 62 are spaced apart at about 2 PET Axial Field Of Views (AFOV's). FIG. 4 illustrates that when phantom 60 is aligned substantially perfectly with an axis 70 of table 46, and axis 70 is substantially normal to a plane 72 of a CT unit 74 and a plane 76 of a PET unit 78, then acquired coronal CT and PET images (80 and 82 respectively) of phantom 60 appear as illustrated in FIG. 4. In a motion section 84 of FIG. 4 multiple bed positions 86 are depicted, to help understand the resulting CT and PET images; the three bed positions 86 are offset slightly to improve readability.

Figure 5:
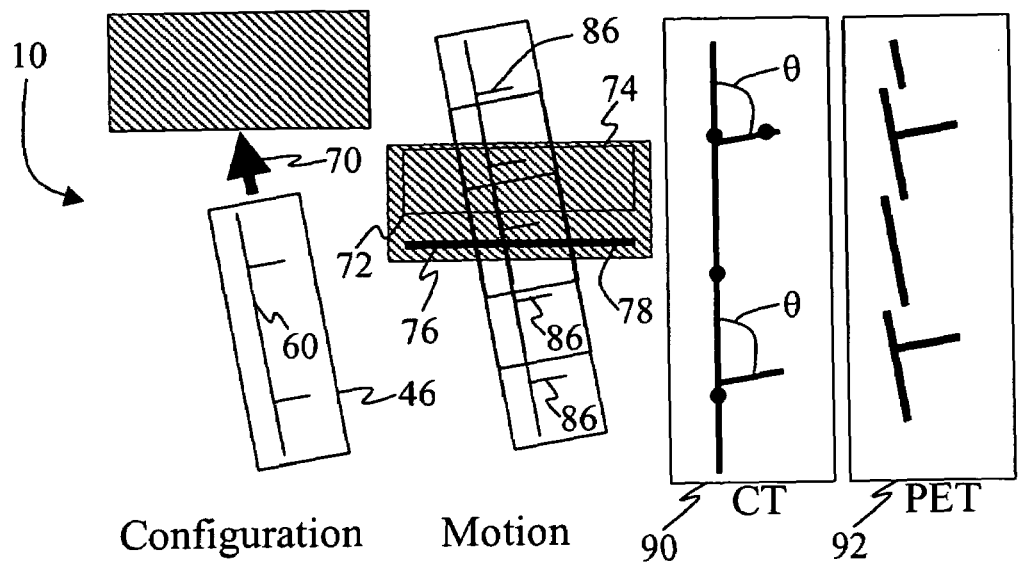
FIG. 5 illustrates the table misaligned with the system shown in FIG. 1.

FIG. 5 illustrates where table 46 is misaligned to both PET unit 76 and CT unit 74 of system 10. In both of an image 90 from a PET scan and an image 92 from a CT scan, the images 90 and 92 have an artifact, but the artifacts are different. PET image 90 has an artifact most evident as a mismatch at the Field Of View (FOV) boundaries. Each individual field of view is an geometrically correct representation of phantom 60 (i.e., arms 62 are perpendicular to body 64 of phantom 60), but the images are not oriented properly and the frames to not align properly at the frame boundaries because of the misalignment of the table axis to the PET frame. By contrast, in CT image 90 body 64 of phantom 60 passes through the same spot on the imaging plane for each slice, so body 64 appears continuous and vertical in the reformatted image. Arms 62 of phantom 60, however, are not imaged in a single CT slice. As a result, arms 62 do not appear perpendicular to the body in the reformatted CT image. Rather arms 62 are at an angle theta to body 64.

Therefore, the herein described methods and apparatus provides a single means to measure both CT-to-PET detector misalignment and CT-to-table misalignment, allowing for accurate alignment of all three components to take place during installation or maintenance of a multi-modal imaging system such as for example but not limited to a combined PET-CT scanner. Additionally, the methods described herein are not limited in use to phantom 60, any phantom or other object can be to determine misalignment.

In one aspect, the method includes taking a set of points identified in a CT image at coordinates $(x_{Ci}, y_{C1}, z_{C1})$, $i \in [1, N]$, and the corresponding points $(x_{P1}, y_{P1}, z_{P1})$, $i \in [1, N]$ identified in a singe-frame PET image and computes a set of eight alignment parameters:

$P_x$ PET-to-table gantry linear misalignment in x (+x to right)
$P_y$ PET-to-table gantry linear misalignment in y (+y downward)
$P_z$ PET-to-table gantry linear misalignment in z (+z away from table)
$\alpha_P$ PET-to-table gantry tilt (+α top rotated forward)
$\beta_P$ PET-to-table gantry yaw (+β right side forward)
$\gamma_P$ PET-to-table (and CT) gantry roll (+γ clockwise viewed from front)
$\beta_T$ Table-to-CT gantry yaw (+β right side forward)
$\alpha_T$ Table-to-CT gantry tilt (+α top rotated forward)

Figure 6:
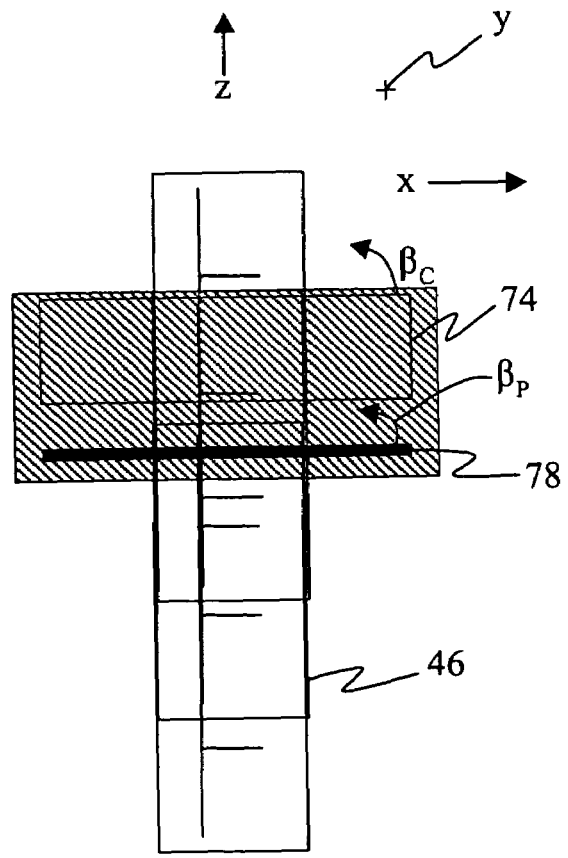
FIG. 6 is a top view of the system shown in FIG. 1.
Figure 7:
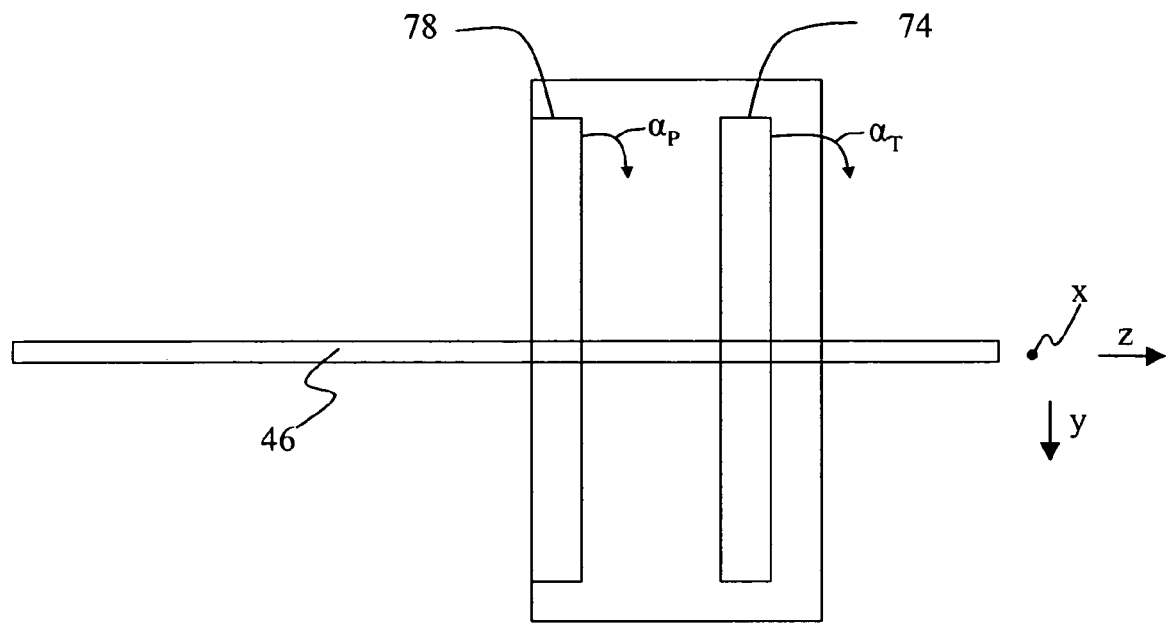
FIG. 7 is a right side view of the system shown in FIG. 1.
Figure 8:
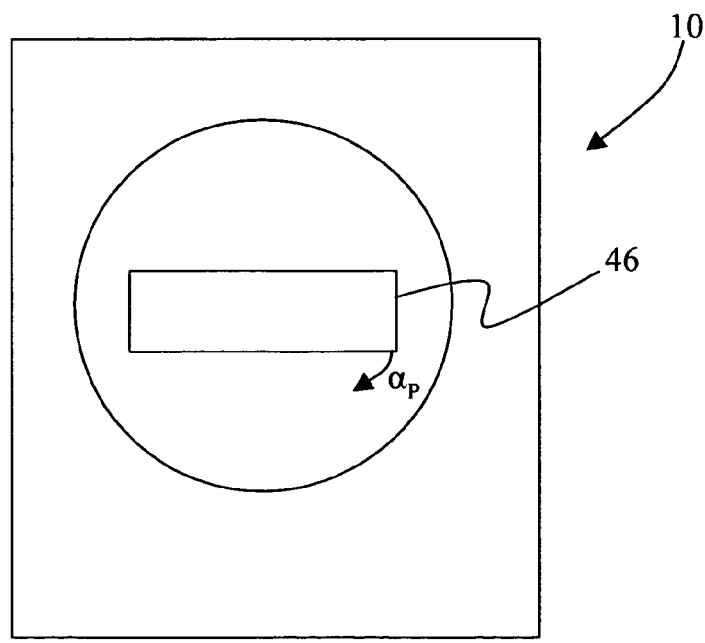
FIG. 8 is a front view of the system shown in FIG. 1.

The algorithm has inputs that are matched CT-PET coordinate pairs (i.e., a collection of points $(x_{C1}, y_{C1}, z_{C1})$ in CT image space matched to the corresponding points $(x_{P1}, y_{P1}, z_{P1})$ in PET image space), and has an output is a set of the eight parameters described above. FIG. 6 is a top view, FIG. 7 is a right side view, and FIG. 8 is a front view of system 10 illustrating the eight parameters.

In one embodiment, the method includes computing sums of the following over all N point pairs: $x_P$, $y_P$, $z_P$, $x_P y_P$, $x_P z_P$, $y_P z_P$, $(x_P)^2$, $(y_P)^2$, $(z_P)^2$, $x_P y_C$, $x_P z_C$, $y_P z_C$, $x_C y_P$, $x_C z_P$, and $y_C z_P$, and populating a transition matrix, T:

$$T \leftarrow \begin{pmatrix} N & 0 & 0 & 0 & -\sum z_P & -\sum y_P & 0 & 0 \\ 0 & N & 0 & \sum z_P & 0 & \sum x_P & 0 & 0 \\ 0 & 0 & N & -\sum y_P & \sum x_P & 0 & \sum x_P & -\sum y_P \\ 0 & \sum z_P & -\sum y_P & \sum y_P^2 + \sum z_P^2 & -\sum x_P y_P & \sum x_P z_P & -\sum x_P y_P & \sum y_P^2 \\ -\sum z_P & 0 & \sum x_P & -\sum x_P y_P & \sum x_P^2 + \sum z_P^2 & \sum y_P z_P & \sum x_P^2 & -\sum x_P y_P \\ -\sum y_P & \sum x_P & 0 & \sum x_P z_P & \sum y_P z_P & \sum x_P^2 + \sum y_P^2 & 0 & 0 \\ 0 & 0 & \sum x_P & -\sum x_P y_P & \sum x_P^2 & 0 & \sum x_P^2 & -\sum x_P y_P \\ 0 & 0 & -\sum y_P & \sum y_P^2 & -\sum x_P y_P & 0 & -\sum x_P y_P & \sum y_P^2 \end{pmatrix}$$

The transition matrix is used to calculate the parameters in accordance with:

$$\begin{pmatrix} \sum x_C - x_P \\ \sum y_C - y_P \\ \sum z_C - z_P \\ \sum z_P y_C - y_P z_C \\ \sum x_P z_C - z_P x_C \\ \sum x_P y_C - y_P x_C \\ \sum x_P z_C - x_P z_P \\ \sum z_P y_P - y_P z_C \end{pmatrix} = \begin{pmatrix} N & 0 & 0 & 0 & -\sum z_P & -\sum y_P & 0 & 0 \\ 0 & N & 0 & \sum z_P & 0 & \sum x_P & 0 & 0 \\ 0 & 0 & N & -\sum y_P & \sum x_P & 0 & \sum x_P & -\sum y_P \\ 0 & \sum z_P & -\sum y_P & \sum y_P^2 + \sum z_P^2 & -\sum x_P y_P & \sum x_P z_P & -\sum x_P y_P & \sum y_P^2 \\ -\sum z_P & 0 & \sum x_P & -\sum x_P y_P & \sum x_P^2 + \sum z_P^2 & \sum y_P z_P & \sum x_P^2 & -\sum x_P y_P \\ -\sum y_P & \sum x_P & 0 & \sum x_P z_P & \sum y_P z_P & \sum x_P^2 + \sum y_P^2 & 0 & 0 \\ 0 & 0 & \sum x_P & -\sum x_P y_P & \sum x_P^2 & 0 & \sum x_P^2 & -\sum x_P y_P \\ 0 & 0 & -\sum y_P & \sum y_P^2 & -\sum x_P y_P & 0 & -\sum x_P y_P & \sum y_P^2 \end{pmatrix} \begin{pmatrix} P_x \\ P_y \\ P_z \\ \alpha_P \\ \beta_P \\ \gamma_P \\ \beta_T \\ \alpha_T \end{pmatrix}$$

Equation (1)

In one embodiment the method includes computing the inverse of the T matrix, $T^1$. In an alternative embodiment, the inverse is not calculated, rather Equation (1) is solved directly by a means such as Gaussian elimination.

In the embodiment using the inverse $T^1$ the method includes calculating the alignment parameters in accordance with:

$$\begin{pmatrix} P_x \\ P_y \\ P_z \\ \alpha_P \\ \beta_P \\ \gamma_P \\ \beta_T \\ \alpha_T \end{pmatrix} \leftarrow T^{-1} \cdot \begin{pmatrix} \sum x_C - x_P \\ \sum y_C - y_P \\ \sum z_C - z_P \\ \sum z_P y_C - y_P z_C \\ \sum x_P z_C - z_P x_C \\ \sum x_P y_C - y_P x_C \\ \sum x_P z_C - x_P z_P \\ \sum z_P y_P - y_P z_C \end{pmatrix} \quad \text{Equation (2)}$$

The above method was derived using small angle approximations such as x=sin x and 1=cos x, and, sometimes, the result is inaccurate because of the approximations. In cases where the above method yields an inaccurate result, the following two step method is useful to improve accuracy. The two step method is to use the above method to generate outputs $P_{x,0}$, $P_{y,0}$, $P_{z,0}$, $\alpha_{P,0}$, $\beta_{P,0}$, $\gamma_{P,0}$, $\beta_{T,0}$ and $\alpha_{T,0}$. Then an updated set of CT points $(x'_C, y'_C, z'_C)$ are generated in accordance with:

$$\begin{pmatrix} x'_C \\ y'_C \\ z'_C \\ 1 \end{pmatrix} = \begin{pmatrix} \cos\beta_{T,0} & \sin\alpha_{T,0}\sin\beta_{T,0} & 0 & 0 \\ 0 & \cos\alpha_{T,0} & 0 & 0 \\ -\sin\beta_{T,0} & \sin\alpha_{T,0}\cos\beta_{T,0} & 1 & 0 \\ 0 & 0 & 0 & 1 \end{pmatrix} \begin{pmatrix} x_C \\ y_C \\ z_C \\ 1 \end{pmatrix}$$

An updated set of PET points is similarly generated according to:

$$\begin{pmatrix} x'_P \\ y'_P \\ z'_P \\ 1 \end{pmatrix} = \begin{pmatrix} 1 & 0 & 0 & 0 \\ 0 & \cos\alpha_{P,0} & \sin\alpha_{P,0} & 0 \\ 0 & -\sin\alpha_{P,0} & \cos\alpha_{P,0} & 0 \\ 0 & 0 & 0 & 1 \end{pmatrix} \begin{pmatrix} \cos\beta_{P,0} & 0 & -\sin\beta_{P,0} & 0 \\ 0 & 1 & 0 & 0 \\ \sin\beta_{P,0} & 0 & \cos\beta_{P,0} & 0 \\ 0 & 0 & 0 & 1 \end{pmatrix}$$

$$\begin{pmatrix} \cos\gamma_{P,0} & -\sin\gamma_{P,0} & 0 & 0 \\ \sin\gamma_{P,0} & \cos\gamma_{P,0} & 0 & 0 \\ 0 & 0 & 1 & 0 \\ 0 & 0 & 0 & 1 \end{pmatrix} \begin{pmatrix} 0 & 0 & 0 & P_{x,0} \\ 0 & 1 & 0 & P_{y,0} \\ 0 & 0 & 1 & P_{z,0} \\ 0 & 0 & 0 & 1 \end{pmatrix} \begin{pmatrix} x_P \\ y_P \\ z_P \\ 1 \end{pmatrix}$$

Using Equation 1 with $(x'_C, y'_C, z'_C)$–$(x'_P, y'_P, z'_P)$ as inputs, yields outputs of $P_{x,1}$, $P_{y,1}$, $P_{z,1}$, $\alpha_{P,1}$, $\beta_{P,1}$, $\gamma_{P,1}$, $\beta_{T,1}$ and $\alpha_{T,1}$. The final alignment parameters are then $$\begin{pmatrix} P_x \\ P_y \\ P_z \\ \alpha_P \\ \beta_P \\ \gamma_P \\ \beta_T \\ \alpha_T \end{pmatrix} = \begin{pmatrix} P_{x,0} \\ P_{y,0} \\ P_{z,0} \\ \alpha_{P,0} \\ \beta_{P,0} \\ \gamma_{P,0} \\ \beta_{T,0} \\ \alpha_{T,0} \end{pmatrix} + \begin{pmatrix} P_{x,1} \\ P_{y,1} \\ P_{z,1} \\ \alpha_{P,1} \\ \beta_{P,1} \\ \gamma_{P,1} \\ \beta_{T,1} \\ \alpha_{T,1} \end{pmatrix}$$

The parameters inform a user or an installer of system 10 as to a table alignment status (i.e., whether or not the table is misaligned with either the first modality unit or the second modality unit, or more typically, both units because the units are substantially aligned to each other). Specifically, $\alpha_T$ and $\beta_T$ parameters are utilized to align the table, and the other six parameters are used to align the CT unit with the PET unit. The installer can then re-align the table (adjust the axis of the table) with the gantry of the imaging system and repeat the herein described methods to verify if the re-aligned system is misaligned or not. Additionally, besides adjusting the table axis, an installer can adjust some aspects of alignment through software. For example, the PET gantry roll can be corrected in the reconstruction software. There is therefore provided efficient and cost effective methods and apparatus for determining component misalignment in multi-modal imaging systems. The herein described methods determine table alignment through parameters $\alpha_T$ and $\beta_T$, while simultaneously determining gantry alignment through parameters $P_x$, $P_y$, $P_z$, $\alpha_P$, $\beta_P$, and $\gamma_P$.

While the invention has been described in terms of various specific embodiments, those skilled in the art will recognize that the invention can be practiced with modification within the spirit and scope of the claims.

What is claimed is:

1. A method of determining component misalignment in a multi-modality imaging system including a first modality unit, a second modality unit, and a table, said method comprising:
    imaging an object with the first modality unit to generate a first image;
    imaging the object with the second modality unit to generate a second image; and
    determining a table alignment status using the first and second images;
    wherein said determining a table alignment status comprises calculating at least one of a first modality unit to table alignment parameter and a second modality unit to table alignment parameter.

2. A method in accordance with claim 1 further comprising making a software correction when the table alignment status is misalignment.

3. A method in accordance with claim 1 further comprising realigning the table when the determined table alignment status is misalignment.

4. A method in accordance with claim 3 further comprising verifying the realignment by:
    imaging the object with the first modality unit to generate a third image;
    imaging the object with the second modality unit to generate a fourth image; and
    determining a table realignment status using the third and fourth images.

5. A method for determining component misalignment in a Positron Emission Tomography/Computed Tomography (PET/CT) system including a PET unit, a CT unit, and a table, said method comprising:
    imaging an object with the PET unit to generate a first image;
    imaging the object with the CT unit to generate a second image; and
    determining a table alignment status using the first and second images;
    wherein said determining a table alignment status comprises calculating at least one of a PET unit to table alignment parameter and a CT unit to table alignment parameter.

6. A method in accordance with claim 5 wherein said determining a table alignment status comprises calculating at least one of a PET unit to table gantry linear misalignment in x parameter, a PET unit to table gantry linear misalignment in y parameter, a PET unit to table gantry linear misalignment in z parameter, a PET unit to table gantry tilt parameter, a PET unit to table gantry yaw parameter, a gantry roll parameter, a CT unit to table gantry tilt parameter, and a PET unit to gantry yaw parameter.

7. A method in accordance with claim 5 wherein said determining a table alignment status comprises calculating a PET unit to table gantry linear misalignment in x parameter, a PET unit to table gantry linear misalignment in y parameter, a PET unit to table gantry linear misalignment in z parameter, a PET unit to table gantry tilt parameter, a PET unit to table gantry yaw parameter, a gantry roll parameter, a CT unit to table gantry tilt parameter, and a PET unit to gantry yaw parameter.

8. A method in accordance with claim 7 wherein said calculating comprises calculating the parameters in accordance with where:
$P_x$ is the PET unit to table gantry linear misalignment in x parameter,
$P_y$ is the PET unit to table gantry linear misalignment in y parameter,
$P_z$ is the PET unit to table gantry linear misalignment in y parameter,
$\alpha_P$ is the PET unit to table gantry tilt parameter,
$\beta_P$ is the PET unit to table gantry yaw parameter,
$\gamma_P$ is the gantry roll parameter,
$\beta_T$ is the CT unit to table gantry yaw parameter,
$\alpha_T$ is the CT unit to table gantry tilt parameter,
$(x_C, y_C, z_C)$ are the coordinates of points in a CT image space matched to corresponding points $(x_P, y_P, z_P)$ in a PET image space, and
N is the number of points in the CT image space that matches points in the PET image space.

9. A method in accordance with claim 8 wherein said calculating further comprises calculating $P_x$, $P_y$, $P_z$, $\alpha_P$, $\beta_P$, $\gamma_P$, $\beta_T$, and $\alpha_T$ by calculating the inverse of Equation (1)

$$\begin{pmatrix} \sum x_C - x_P \\ \sum y_C - y_P \\ \sum z_C - z_P \\ \sum z_P y_C - y_P z_C \\ \sum x_P z_C - z_P x_C \\ \sum x_P y_C - y_P x_C \\ \sum x_P z_C - x_P z_P \\ \sum z_P y_P - y_P z_C \end{pmatrix} = \begin{pmatrix} N & 0 & 0 & 0 & -\sum z_P & -\sum y_P & 0 & 0 \\ 0 & N & 0 & \sum z_P & 0 & \sum x_P & 0 & 0 \\ 0 & 0 & N & -\sum y_P & \sum x_P & 0 & \sum x_P & -\sum y_P \\ 0 & \sum z_P & -\sum y_P & \sum y_P^2 + \sum z_P^2 & -\sum x_P y_P & \sum x_P z_P & -\sum x_P y_P & \sum y_P^2 \\ -\sum z_P & 0 & \sum x_P & -\sum x_P y_P & \sum x_P^2 + \sum z_P^2 & \sum y_P z_P & \sum x_P^2 & -\sum x_P y_P \\ -\sum y_P & \sum x_P & 0 & \sum x_P z_P & \sum y_P z_P & \sum x_P^2 + \sum y_P^2 & 0 & 0 \\ 0 & 0 & \sum x_P & -\sum x_P y_P & \sum x_P^2 & 0 & \sum x_P^2 & -\sum x_P y_P \\ 0 & 0 & -\sum y_P & \sum y_P^2 & -\sum x_P y_P & 0 & -\sum x_P y_P & \sum y_P^2 \end{pmatrix} \begin{pmatrix} P_x \\ P_y \\ P_z \\ \alpha_P \\ \beta_P \\ \gamma_P \\ \beta_T \\ \alpha_T \end{pmatrix}$$

50

$$\begin{pmatrix} N & 0 & 0 & 0 & -\sum z_P & -\sum y_P & 0 & 0 \\ 0 & N & 0 & \sum z_P & 0 & \sum x_P & 0 & 0 \\ 0 & 0 & N & -\sum y_P & \sum x_P & 0 & \sum x_P & -\sum y_P \\ 0 & \sum z_P & -\sum y_P & \sum y_P^2 + \sum z_P^2 & -\sum x_P y_P & \sum x_P z_P & -\sum x_P y_P & \sum y_P^2 \\ -\sum z_P & 0 & \sum x_P & -\sum x_P y_P & \sum x_P^2 + \sum z_P^2 & \sum y_P z_P & \sum x_P^2 & -\sum x_P y_P \\ -\sum y_P & \sum x_P & 0 & \sum x_P z_P & \sum y_P z_P & \sum x_P^2 + \sum y_P^2 & 0 & 0 \\ 0 & 0 & \sum x_P & -\sum x_P y_P & \sum x_P^2 & 0 & \sum x_P^2 & -\sum x_P y_P \\ 0 & 0 & -\sum y_P & \sum y_P^2 & -\sum x_P y_P & 0 & -\sum x_P y_P & \sum y_P^2 \end{pmatrix}$$

10. A method in accordance with claim 5 further comprising making a software correction when the determined table misalignment status is misalignment.

11. A method in accordance with claim 5 further comprising realigning the table when the determined table alignment status is misalignment.

12. A method in accordance with claim 11 further comprising verifying the realignment by:
 imaging the object with the PET unit to generate a third image;
 imaging the object with the CT unit to generate a fourth image; and
 determining a table realignment status using the third and fourth images.

13. A method for installing a Positron Emission Tomography/Computed Tomography (PET/CT) system at a desired location, the PET/CT system including a PET unit, a CT unit, and a table, said method comprising:
 positioning the PET/CT system at the desired location wherein the table has an axis extending through the system;
 imaging an object with the PET unit to generate a first image;
 imaging the object with the CT unit to generate a second image; and
 adjusting the table axis based upon the first and second images;
 calculating at least one of a PET unit to table alignment parameter and a CT unit to table alignment parameter based on the first and second images, said adjusting the table axis comprises adjusting the table axis based upon the calculated parameter.

14. A method in accordance with claim 13 further comprising calculating at least one of a PET unit to table gantry linear misalignment in x parameter, a PET unit to table gantry linear misalignment in y parameter, a PET unit to table gantry linear misalignment in z parameter, a PET unit to table gantry tilt parameter, a PET unit to table gantry yaw parameter, a gantry roll parameter, a CT unit to table gantry tilt parameter, and a PET unit to gantry yaw parameter, said adjusting the table axis comprises adjusting the table axis based upon the calculated parameter.

15. A method in accordance with claim 13 further comprising calculating a PET unit to table gantry linear misalignment in x parameter, a PET unit to table gantry linear misalignment in y parameter, a PET unit to table gantry linear misalignment in z parameter, a PET unit to table gantry tilt parameter, a PET unit to table gantry yaw parameter, a gantry roll parameter, a CT unit to table gantry tilt parameter, and a PET unit to gantry yaw parameter, said adjusting the table axis comprises adjusting the table axis based upon the calculated parameters.

16. A method in accordance with claim 15 wherein said calculating comprises calculating the parameters in accordance with $$\begin{pmatrix} \sum x_C - x_P \\ \sum y_C - y_P \\ \sum z_C - z_P \\ \sum z_P y_C - y_P z_C \\ \sum x_P z_C - z_P x_C \\ \sum x_P y_C - y_P x_C \\ \sum x_P z_C - x_P z_P \\ \sum z_P y_P - y_P z_C \end{pmatrix} = $$

Equation (1)

$$\begin{pmatrix} N & 0 & 0 & 0 & -\sum z_P & -\sum y_P & 0 & 0 \\ 0 & N & 0 & \sum z_P & 0 & \sum x_P & 0 & 0 \\ 0 & 0 & N & -\sum y_P & \sum x_P & 0 & \sum x_P & -\sum y_P \\ 0 & \sum z_P & -\sum y_P & \sum y_P^2 + \sum z_P^2 & -\sum x_P y_P & \sum x_P z_P & -\sum x_P y_P & \sum y_P^2 \\ -\sum z_P & 0 & \sum x_P & -\sum x_P y_P & \sum x_P^2 + \sum z_P^2 & \sum y_P z_P & \sum x_P^2 & -\sum x_P y_P \\ -\sum y_P & \sum x_P & 0 & \sum x_P z_P & \sum y_P z_P & \sum x_P^2 + \sum y_P^2 & 0 & 0 \\ 0 & 0 & \sum x_P & -\sum x_P y_P & \sum x_P^2 & 0 & \sum x_P^2 & -\sum x_P y_P \\ 0 & 0 & -\sum y_P & \sum y_P^2 & -\sum x_P y_P & 0 & -\sum x_P y_P & \sum y_P^2 \end{pmatrix} \begin{pmatrix} P_x \\ P_y \\ P_z \\ \alpha_P \\ \beta_P \\ \gamma_P \\ \beta_T \\ \alpha_T \end{pmatrix}$$

where:
 $P_x$ is the PET unit to table gantry linear misalignment in x parameter,
 $P_y$ is the PET unit to table gantry linear misalignment in y parameter, $P_z$ is the PET unit to table gantry linear misalignment in y parameter,
$\alpha_P$ is the PET unit to table gantry tilt parameter,
$\beta_P$ is the PET unit to table gantry yaw parameter,
$\gamma_P$ is the gantry roll parameter,
$\beta_T$ is the CT unit to table gantry yaw parameter,
$\alpha_T$ is the CT unit to table gantry tilt parameter,
$(x_C, y_C, z_C)$ are the coordinates of points in a CT image space matched to corresponding points $(x_P, y_P, z_P)$ in a PET image space, and
N is the number of points in the CT image space that matches points in the PET space.

17. A method in accordance with claim 16 further comprising calculating the inverse of where N is the number of points in a first modality image space that match points in a second modality space, and $(x_P, y_P, z_P)$ are one of coordinates of points in an image space of the first image and coordinates of points in an image space of the second image.

19. A system in accordance with claim 18 wherein said computer further configured to calculate at least one of a first modality unit to table alignment parameter and a second modality unit to table alignment parameter using the matrix.

20. A system in accordance with claim 18 wherein said computer further configured to calculate the inverse (I) to the matrix.

21. A computer readable medium encoded with a program configured to instruct a computer to:

$$\begin{pmatrix} N & 0 & 0 & 0 & -\sum z_P & -\sum y_P & 0 & 0 \\ 0 & N & 0 & \sum z_P & 0 & \sum x_P & 0 & 0 \\ 0 & 0 & N & -\sum y_P & \sum x_P & 0 & \sum x_P & -\sum y_P \\ 0 & \sum z_P & -\sum y_P & \sum y_P^2 + \sum z_P^2 & -\sum x_P y_P & \sum x_P z_P & -\sum x_P y_P & \sum y_P^2 \\ -\sum z_P & 0 & \sum x_P & -\sum x_P y_P & \sum x_P^2 + \sum z_P^2 & \sum y_P z_P & \sum x_P^2 & -\sum x_P y_P \\ -\sum y_P & \sum x_P & 0 & \sum x_P z_P & \sum y_P z_P & \sum x_P^2 + \sum y_P^2 & 0 & 0 \\ 0 & 0 & \sum x_P & -\sum x_P y_P & \sum x_P^2 & 0 & \sum x_P^2 & -\sum x_P y_P \\ 0 & 0 & -\sum y_P & \sum y_P^2 & -\sum x_P y_P & 0 & -\sum x_P y_P & \sum y_P^2 \end{pmatrix}$$

18. A multi modality imaging system comprising:
a first modality unit comprising a bore therethrough;
a second modality unit comprising a bore therethrough;
a table positioned to move at least partially through said first modality unit bore and said second modality bore; and
a computer operationally coupled to said first and second modality units, said computer configured to:
image an object with the first modality unit to generate a first image;
image the object with the second modality unit to generate a second image; and
calculate a matrix according to image an object with a multi-modal imaging system in a first modality to generate a first image;

image the object with the multi-modal imaging system in a second modality to generate a second image; and determine a table alignment status using the first and second images;

wherein said program further configured to instruct the computer to calculate a matrix according to $$\begin{pmatrix} N & 0 & 0 & 0 & -\sum z_P & -\sum y_P & 0 & 0 \\ 0 & N & 0 & \sum z_P & 0 & \sum x_P & 0 & 0 \\ 0 & 0 & N & -\sum y_P & \sum x_P & 0 & \sum x_P & -\sum y_P \\ 0 & \sum z_P & -\sum y_P & \sum y_P^2 + \sum z_P^2 & -\sum x_P y_P & \sum x_P z_P & -\sum x_P y_P & \sum y_P^2 \\ -\sum z_P & 0 & \sum x_P & -\sum x_P y_P & \sum x_P^2 + \sum z_P^2 & \sum y_P z_P & \sum x_P^2 & -\sum x_P y_P \\ -\sum y_P & \sum x_P & 0 & \sum x_P z_P & \sum y_P z_P & \sum x_P^2 + \sum y_P^2 & 0 & 0 \\ 0 & 0 & \sum x_P & -\sum x_P y_P & \sum x_P^2 & 0 & \sum x_P^2 & -\sum x_P y_P \\ 0 & 0 & -\sum y_P & \sum y_P^2 & -\sum x_P y_P & 0 & -\sum x_P y_P & \sum y_P^2 \end{pmatrix}$$

$$\begin{pmatrix} N & 0 & 0 & 0 & -\sum z_P & -\sum y_P & 0 & 0 \\ 0 & N & 0 & \sum z_P & 0 & \sum x_P & 0 & 0 \\ 0 & 0 & N & -\sum y_P & \sum x_P & 0 & \sum x_P & -\sum y_P \\ 0 & \sum z_P & -\sum y_P & \sum y_P^2 + \sum z_P^2 & -\sum x_P y_P & \sum x_P z_P & -\sum x_P y_P & \sum y_P^2 \\ -\sum z_P & 0 & \sum x_P & -\sum x_P y_P & \sum x_P^2 + \sum z_P^2 & \sum y_P z_P & \sum x_P^2 & -\sum x_P y_P \\ -\sum y_P & \sum x_P & 0 & \sum x_P z_P & \sum y_P z_P & \sum x_P^2 + \sum y_P^2 & 0 & 0 \\ 0 & 0 & \sum x_P & -\sum x_P y_P & \sum x_P^2 & 0 & \sum x_P^2 & -\sum x_P y_P \\ 0 & 0 & -\sum y_P & \sum y_P^2 & -\sum x_P y_P & 0 & -\sum x_P y_P & \sum y_P^2 \end{pmatrix}$$

15 where N is the number of points in a first modality image space that match points in a second modality space, and $(X_p, y_p, Z_p)$ are one of coordinates of points in an image space of the first image and coordinates of points in an image space of the second image.

\* \* \* \* \*